US012766312B2

(12) United States Patent
Epstein et al.

(10) Patent No.: US 12,766,312 B2
(45) Date of Patent: Oct. 20, 2026

(54) DEFIBRILLATION SYSTEM HAVING DEFORMABLE PADDLE HEAD

(71) Applicant: USB Medical, Ltd., Hatboro, PA (US)

(72) Inventors: Stephen T Epstein, Newtown, PA (US); John J. Sinisi, Warminster, PA (US); Jesse Sinisi, Warminster, PA (US)

(73) Assignee: U58 Medical Ltd., Hatboro, PA (US)

( * ) Notice: Subject to any disclaimer, the term of this patent is extended or adjusted under 35 U.S.C. 154(b) by 415 days.

(21) Appl. No.: 18/349,121

(22) Filed: Jul. 7, 2023

(65) Prior Publication Data

US 2024/0009447 A1 Jan. 11, 2024

Related U.S. Application Data

(60) Provisional application No. 63/359,813, filed on Jul. 9, 2022.

(51) Int. Cl.
*A61N 1/04* (2006.01)
*A61N 1/39* (2006.01)

(52) U.S. Cl.
CPC ........... *A61N 1/046* (2013.01); *A61N 1/3968* (2013.01)

(58) Field of Classification Search
CPC .... A61N 1/046; A61N 1/0587; A61N 1/3904; A61N 1/3968
See application file for complete search history.

(56) References Cited

U.S. PATENT DOCUMENTS

| | | | |
|---|---|---|---|
| 2,985,172 | A | 5/1961 | Jones |
| 3,389,703 | A | 6/1968 | Criswell et al. |
| 3,670,736 | A | 6/1972 | Panico |
| 4,554,910 | A | 11/1985 | Lally |
| 4,681,112 | A | 7/1987 | Jones et al. |
| 4,705,044 | A | 11/1987 | Deluhery et al. |
| 4,852,585 | A | 8/1989 | Heath |
| 5,645,522 | A | 7/1997 | Lurie et al. |
| 5,904,711 | A | 5/1999 | Flom et al. |
| 6,097,987 | A | 8/2000 | Milani |
| 6,156,060 | A | 12/2000 | Roy et al. |
| 6,360,125 | B1 | 3/2002 | Weil et al. |
| 6,721,597 | B1 | 4/2004 | Bardy et al. |

(Continued)

FOREIGN PATENT DOCUMENTS

| | | | |
|---|---|---|---|
| EP | 0353341 | A1 | 2/1990 |
| WO | WO 2007/051648 | A1 | 5/2007 |

*Primary Examiner* — Amanda K Hulbert
(74) *Attorney, Agent, or Firm* — LaMorte & Associates P.C.

(57) ABSTRACT

A defibrillation system having a paddle assembly with a paddle head and handle. The paddle head includes an enlarged support pad that is attached to the handle via a flexible neck. Both the enlarged support pad and the neck are formed from a thermoplastic elastomer and are highly flexible. A contact electrode is attached to the enlarged support pad. The contact electrode conducts electrical current to the heart. The contact electrode is thin and can deform with the enlarged support pad. The contact electrode receives electrical current through a conducive core element. The conductive core element extends through the handle and into the flexible paddle head, wherein the conductive core element is electrically coupled to the contact electrode via a terminal lead within the flexible paddle head.

13 Claims, 4 Drawing Sheets

(56) References Cited

U.S. PATENT DOCUMENTS

| | | | | |
|---|---|---|---|---|
| 6,950,705 | B2 | 9/2005 | Bardy et al. | |
| 6,961,611 | B2 | 11/2005 | Dupelle | |
| 6,969,259 | B2 | 11/2005 | Pastrick et al. | |
| 7,016,727 | B2 | 3/2006 | Powers et al. | |
| 7,245,974 | B2 | 7/2007 | Dupelle et al. | |
| 8,452,393 | B1 * | 5/2013 | Epstein | A61N 1/0587 607/142 |
| 9,314,610 | B2 * | 4/2016 | Khuon | A61N 1/046 |
| 10,682,511 | B2 * | 6/2020 | Epstein | A61N 1/0587 |
| 2002/0042629 | A1 | 4/2002 | Bardy et al. | |
| 2002/0062144 | A1 | 5/2002 | Zadini et al. | |
| 2002/0103510 | A1 | 8/2002 | Bardy et al. | |
| 2003/0045905 | A1 | 3/2003 | Daynes et al. | |
| 2003/0078470 | A1 | 4/2003 | Borst et al. | |
| 2003/0191501 | A1 * | 10/2003 | Miller | A61N 1/0587 607/5 |
| 2004/0088035 | A1 | 5/2004 | Guenst et al. | |
| 2004/0162588 | A1 | 8/2004 | Watanabe et al. | |
| 2004/0186545 | A1 | 9/2004 | Rosero et al. | |
| 2004/0199236 | A1 | 10/2004 | Laske et al. | |
| 2004/0210259 | A1 | 10/2004 | Rock et al. | |
| 2004/0230231 | A1 | 11/2004 | Thacker et al. | |
| 2005/0240232 | A9 | 10/2005 | Bardy et al. | |
| 2006/0004416 | A1 | 1/2006 | Bardy et al. | |
| 2006/0025826 | A1 | 2/2006 | Erlinger et al. | |
| 2006/0259081 | A1 | 11/2006 | Vaisnys et al. | |
| 2007/0233197 | A1 | 10/2007 | Jung et al. | |
| 2007/0299473 | A1 | 12/2007 | Matos | |
| 2008/0033495 | A1 | 2/2008 | Kumar | |
| 2011/0009936 | A1 | 1/2011 | Katsunori et al. | |
| 2014/0155968 | A1 | 6/2014 | Govea et al. | |
| 2014/0194965 | A1 | 7/2014 | Osypka | |
| 2018/0036528 | A1 | 2/2018 | Epstein et al. | |

* cited by examiner

DEFIBRILLATION SYSTEM HAVING DEFORMABLE PADDLE HEAD

RELATED APPLICATIONS

This supplication claims the benefit of U.S. Provisional Patent Application No. 63/359,813, filed Jul. 9, 2022.

BACKGROUND OF THE INVENTION

1. Field of the Invention

In general, the present invention relates to defibrillation paddles. More particularly, the present invention relates to defibrillation paddles that are used during open and minimally invasive procedures wherein the defibrillation paddle is brought into direct contact with the tissue of the heart.

2. Prior Art Description

It is known that a heart muscle that has stopped beating or is beating erratically can sometimes be caused to beat normally by passing an electrical current through the tissue of the heart. The science of applying an electrical current to the heart is known as defibrillation and has been evolving for many years.

Defibrillator systems are specifically designed to pass an electrical current into a patient's heart. In the field of defibrillation, there are non-intrusive defibrillator paddles and intrusive defibrillator paddles. Non-intrusive defibrillator paddles have two electrodes that attach to the skin of a patient. The non-intrusive defibrillator paddles pass electricity through the body from one external point to another. Such non-intrusive defibrillator paddles are used by rescue workers, paramedics, and the like to revive a person whose heart has stopped.

Intrusive defibrillator paddles are used by physicians primarily in the operating room of hospitals. During many surgical procedures, a patient's heart may be temporarily stopped. In such situations, the patient's blood flow is transferred to an external pump. Once the surgical procedure is complete, a defibrillator paddle is commonly used to restart the heart. When the heart muscle itself is exposed, defibrillator paddles can be touched directly to the heart muscle. A small jolt of electricity is then passed through the tissue of the heart muscle to restart the heartbeat. Since the electricity is being applied directly to the heart muscle, low currents of electricity are used. However, even these low currents of electricity can result in some heart muscle tissue becoming burned in the areas of contact with the defibrillator paddles, especially if there is not good contact with the heart tissue.

One way to reduce the potential of damage to the heart muscle is to use a defibrillation system that touches the heart with only a single paddle. If only one paddle touches the heart, it is easier for a physician to bring that single paddle into proper contact with the heart.

In the prior art, defibrillator systems have been made that use only one paddle to contact the heart. In such systems, a patient is placed upon a conductive pad. A single paddle is provided. Both the single paddle and the conductive pad are connected to the same defibrillator system to create a circuit. The single paddle is then touched to the tissue of the heart. Electricity passes through the heart, through the back of the body and to the conductive pad. Since only one paddle is used, the chances that one paddle will be poorly positioned is reduced by half, as compared to a two paddle system.

Such prior art defibrillation systems are exemplified by Japanese Reference No. JP2001121885, entitled Defibrillating Electrode And Defibrillation System; U.S. Pat. No. 8,452,393 to Epstein, entitled Defibrillation Paddle Structure And Its Associated Method Of Use, and U.S. Pat. No. 10,682,511 to Epstein, entitled Defibrillator For Minimally Invasive Surgical Procedures.

When surgery is performed on the heart, the surgery can often be defined as either open heart surgery or minimally invasive surgery. During open heart surgery, the ribcage is opened at the sternum by the surgeon to expose the heart. This type of surgery requires a long and painful recovery period as the ribcage heals. As surgical procedures evolve, an increasing number of surgical procedures on the heart are being performed using minimally invasive techniques. When minimally invasive surgical techniques are used, the ribcage remains largely undisturbed. Small entrance holes, referred to as working ports, are formed between the ribs of the ribcage that enable elongated surgical instruments to be advanced toward the heart in the chest cavity. However, this presents certain problems, especially when it comes to defibrillation.

When the paddle head of a defibrillator system contacts the muscle tissue of the heart, the largest contact area possible is desired. If only a small contact area exists, all of the electrical current passing into the heart is forced to travel through the small area of tissue in contact with the defibrillator paddle head. This concentrates the electricity and can cause tissue burning and damage to the heart tissue. A large area of contact is desired because it distributes the flow of electrical current and is, therefore, less likely to cause burning. The key to avoiding tissue damage made by a defibrillator paddle is to have uniform contact between the paddle and the tissue of the heart muscle. To further complicate matters, a physician may decide to shock the heart at a specific spot. That location may be at the vertical apex, along the right ventricle or along the left ventricle. The doctor must maneuver the defibrillator paddle to that portion of the heart while still maintaining a flush contact between the defibrillator paddle and the tissue of the heart. If there is not a flush contact, the odds greatly increase that the defibrillator paddle may cause an electrical burn. Furthermore, without a flush contact, the defibrillator paddle may fail to affect the heart muscle in the desired manner.

A further problem exists because, in order to use a defibrillation paddle in a minimally invasive surgical technique, the paddle head must be small and of the proper shape and construction to reach the heart and work as intended. Current configurations of paddle heads have round shapes with complicated assemblies on the back side of the paddle head that take up valuable space. This makes such paddle heads expensive to manufacture and too large for most current minimally invasive procedures.

A need therefore exists for an improved defibrillation paddle design with an improved paddle shape that can be economically constructured, is more reliable than prior art paddles and functions better than prior art defibrillation paddles when used during minimally invasive procedures. These needs are met by the present invention as described and claimed below.

SUMMARY OF THE INVENTION

The present invention is a defibrillation system that utilizes an improved paddle assembly with an elliptical or oval shape and a uniquely simplified flexible construction. The paddle assembly has a paddle head that physically touches the heart during the defibrillation procedure. The paddle head is manipulated using a handle. The paddle head includes an enlarged support pad that is attached to the handle via a flexible neck. Both the enlarged support pad and the neck are formed from a thermoplastic elastomer and are highly flexible. Due to the flexibility of the material, both the enlarged support pad and the neck can be advanced through a small incision during a minimally invasive procedure.

A contact electrode is attached to the enlarged support pad. The contact electrode conducts electrical current to the heart. The enlarged support pad is thin and can deform with the enlarged support pad. The contact electrode receives electrical current through a conducive core element. The conductive core element extends through the handle and into the flexible paddle head, wherein the conductive core element is electrically coupled to the contact electrode via a terminal lead within the flexible paddle head.

The flexible neck is molded in a position where the flexible neck extends out of the side of the enlarged support pad. This low-profile configuration is an important advantage for minimally invasive procedures. In addition, the elliptical or oval shape of the enlarged support pad enables the overall paddle head to be narrower side to side while maintaining a larger contact area for proper electrical disbursement. In this manner, a contact area can be maintained that is equivalent to a rounder head configuration that would not fit through the same sized surgical entry point. This width advantage could be the deciding factor between selecting between a minimally Invasive approach and a far more invasive open approach that would result is a longer recovery time, larger scars, and more possibilities for infection.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention defibrillation paddle can be embodied in many ways, the embodiment illustrated shows only one paddle design. The embodiment is selected in order to set forth one of the best modes contemplated for the invention. The illustrated embodiment, however, is merely exemplary and should not be considered a limitation when interpreting the scope of the appended.

Figure 1:
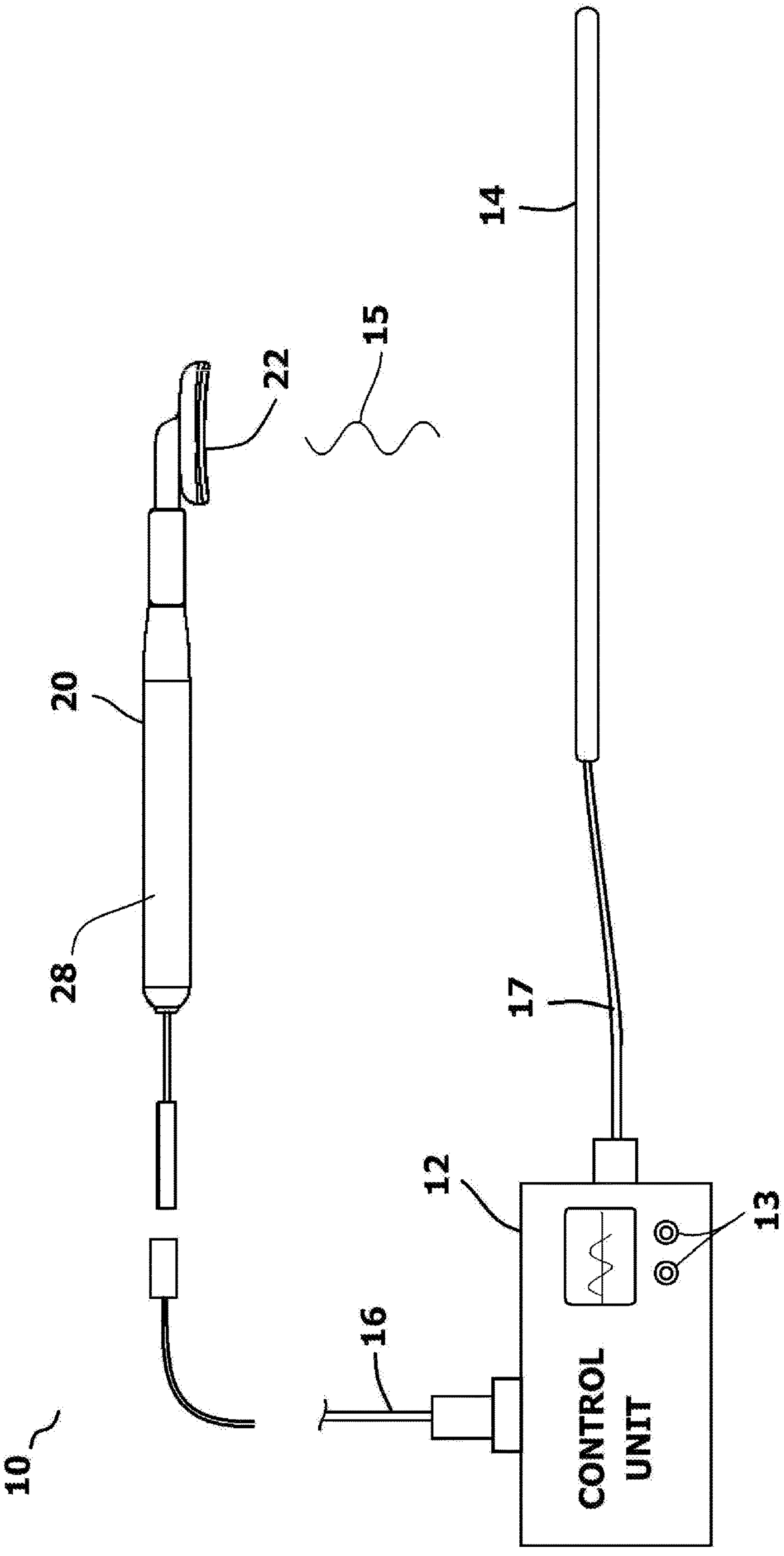
FIG. 1 shows an exemplary embodiment of a defibrillation system.

Referring to FIG. 1, there is shown an exemplary embodiment of a defibrillation system 10 in accordance with the present invention. The defibrillation system 10 consists of a control unit 12 that controls the electrical current and waveform that will be passed through the heart muscle during the defibrillation procedure. The control unit 12 has adjustable controls 13 and safeguards common in the industry. There are several defibrillation systems that are commercially available. The control unit of most prior art defibrillation systems can be adapted for use as part of the present invention defibrillation system 10.

The control unit 12 creates the waveform 15 that is applied to the heart. To apply the waveform 15 to the heart, an electrical pathway must be created that passes through the heart. To create the needed electrical pathway, a conductive pad 14 is provided. The conductive pad 14 is placed under a prone patient in a position that is below the heart in the vertical plane. The conductive pad 14 contacts the skin of the patient across a wide contact area. The conductive pad 14 is connected to the control unit 12 by a first flexible terminal wire 17.

The waveform 15 from the control unit 12 is applied to the patient using a paddle assembly 20. The paddle assembly 20 can be selectively attached to the control unit 12 via the second flexible terminal wire 16. The paddle assembly 20 has a contact electrode 22. The control unit 12 creates an electrical bias between the contact electrode 22 on the paddle assembly 20 and the conductive pad 14. Accordingly, when both the conductive pad 14 and the contact electrode 22 of the paddle assembly 20 touch a patient, current waveform 15 can flow through the patient between these surfaces.

In practice, the conductive pad 14 is externally placed under a prone patient. As part of a minimally invasive procedure, the paddle assembly 20 is manipulated by a surgeon inside the body so that the contact electrode 22 contacts the heart in a particular place. The defibrillation system 10 is then activated so that the current waveform 15 passes into the paddle assembly 20, through the contact electrode 22, through the heart, and through the portion of the patient's body between the heart and the conductive pad 14.

Figure 2:
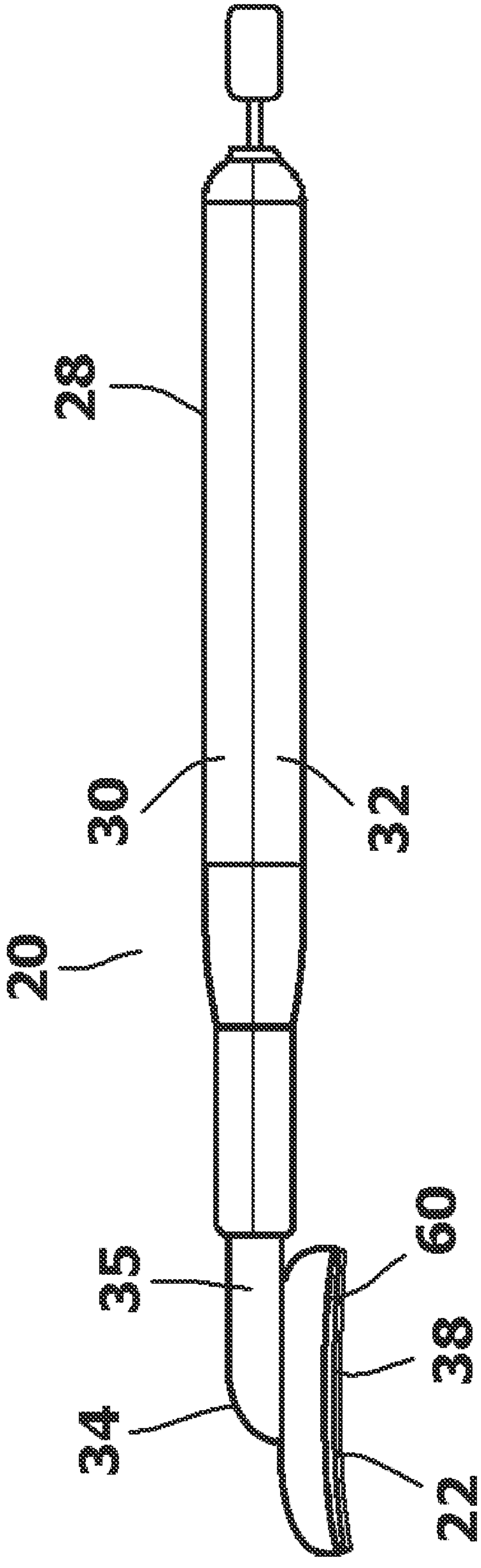
FIG. 2 is an enlarged view of the paddle assembly used in the exemplary embodiment of FIG. 1.
Figure 3:
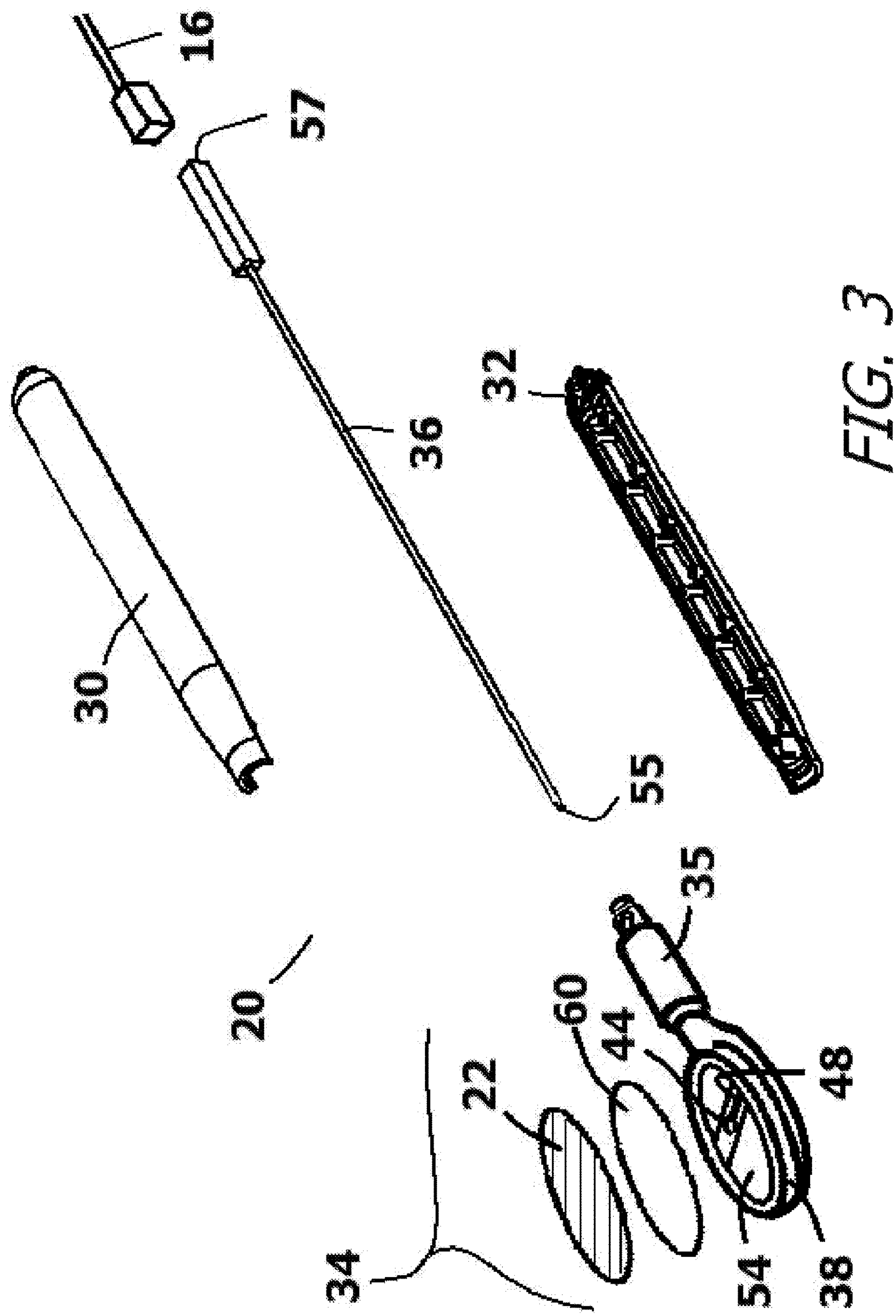
FIG. 3 is an exploded perspective view of the paddle assembly shown in FIG. 2.
Figure 4:
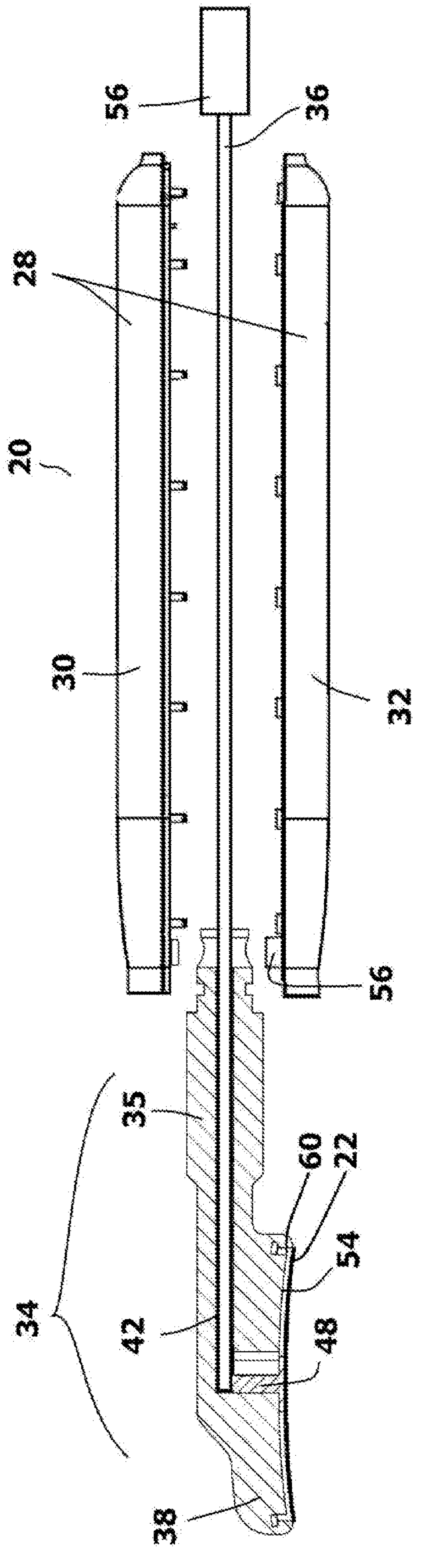
FIG. 4 is an exploded and partially cross-sectioned side view of the paddle assembly used in FIG. 2.

Referring to FIG. 2, FIG. 3 and FIG. 4, the details for the structure of the paddle assembly 20 are shown. The paddle assembly 20 has handle 28 to facilitate the manual manipulation of the paddle assembly 20. The handle 28 can be straight, or it can be ergonomically shaped to fit comfortably in a physician's hand. The handle 28 can have many lengths, wherein a physician selects the handle length depending upon the size of the patient and the intricacies of the procedure. In the shown embodiment, the paddle assembly 20 is one that can be used in either a minimally invasive procedure or an open invasive procedure. The paddle assembly 20 and has a handle 28 that will not block access of other instruments through a small incision. It will be understood that the handle 28 can be larger if used in open chest procedures.

The handle 28 has a two-part clamshell design, wherein the handle 28 has two halves 30, 32. The two halves 30, 32 are molded from a robust plastic and are textured to prevent a grip from slipping. When assembled, the handle 28 has a first end 29 and an opposite second end 31. The two halves 30, 32 are designed to engage and retain both the paddle assembly 20 and a conductive core element 36. The handle 28 supports the paddle assembly 20 so that the paddle assembly 20 extends from the first end 29 of the handle 28. The conductive core element 36 extends through the handle 28 from the paddle assembly 20 to the second end 31 of the handle 28.

The paddle assembly 20 includes a paddle head 34 that is disposed at the end of a flexible neck 35. The flexible neck 35 is concentrically aligned with the handle 28 and extends into the first end 29 of the handle 28. The low cost one-piece flexible neck 35 acts as a cantilever and self-centering spring that supports the paddle head 34 and attaches the paddle head but also allows it to be flexed into any position around the heart.

The paddle head 34 contains an enlarged support pad 38 that is generally circular and optimally elliptical in shape. The flexible neck 35 extends from the peripheral side of the enlarged support pad 38. In this manner, the presence of the flexible neck 35 does increase the thickness of the enlarged support pad 38 or the overall thickness of the paddle head 34. Both the enlarged support pad 38 and the flexible neck 35 are unistucturally molded from a curable silicone or another soft thermoplastic elastomer. Accordingly, depending upon the flexibility of the contact electrode 22 being supported, the enlarged support pad 38 can be deformed by applying sufficient forces to the structure. If the contact electrode 22 is relatively stiff, small deflections can be made that will assist the paddle head 34 in passing into an incision. If the contact electrode 22 is a highly flexible foil or similar conductive surface, then the enlarged support pad 38 can be rolled into a size just wider than that of the flexible neck 35. In this manner, the entire paddle assembly 20, up to the handle 28, can be advanced through a narrow incision that is only slightly larger than the diameter of the flexible neck 35. Likewise, the flexible neck 35 can be bent using the application of external forces. The ability of the enlarged support pad 38 and the flexible neck 35 to bend and deform is very useful in inserting the overall paddle assembly 20 through a small surgical incision and positioning the paddle head 34 properly in relation to the heart during a surgical procedure.

An open conduit 42 extends through the flexible neck 35 and into the enlarged support pad 38. The open conduit 42 is sized to receive a section of the conductive core element 36. A traverse hole 44 is formed in the enlarged support pad 38 at or near its center. The traverse hole 44 intersects the open conduit 42 at a perpendicular. A conductive contact terminal 48 extends through the traverse hole 44. The conductive contact terminal 48 intersects the open conduit 42. The opposite end of the conductive contact terminal 48 terminates at a face surface 54 of the enlarged support pad 38. Accordingly, the conductive contact terminal 48 connects the open conduit 42 to the face surface 54 of the paddle head 34.

The conductive core element 36 extends into the open conduit 42 of the paddle head 34. The conductive core element 36 has a first end 55 and an opposite second end 57. The first end 55 of the conductive core element 36 contacts, and electrically interconnects, with the contact terminal 48 that extends through the traverse hole 44. The second end 57 of the conductive core element 36 extends out of the open conduit 42 in the paddle head 34 and through the handle 28. The second end 57 of the conductive core element 36 terminates with a connector plug 58 beyond the second end 31 of the handle 28. The connector plug 58 attaches to the second terminal wire 16 of the overall defibrillation system 10.

Within the handle 28 is a connector 56. The connector 56 engages the conductive core element 36 as the two halves 30, 32 of the handle 28 are joined around the conductive contact terminal 48. The connector 56 locks the conductive core element 36 in a fixed position relative to the handle 28.

In the handle 28, the conductive core element 36 is locked into a fixed position. However, the conductive core element 36 also extends through the flexible neck 35. The conductive core element 36 itself is also flexible. In this manner, when the paddle head 34 is distorted, the conductive core element 36 can bend within the flexible neck 35 to be better positioned against the heart.

Within the paddle head 34, the conductive core element 36 terminates at the conductive contact terminal 48, wherein both the conductive core element 36 and the conductive contact terminal 48 electrically interconnect.

The conductive contact terminal 48 extends through the support pad 38 to the face surface 54 of the paddle head 34. The conductive contact terminal 48 electrically connects to a conductive support 60. The conductive support 60 can either be a removable element or can be molded into the paddle head 34. The conductive support 60 provides direct support to the contact electrode 22. The conductive support 60 is generally the same size as the contact electrode 22. In this manner, the full contact electrode 22 will receive an evenly distributed charge from the conductive support 60. It is the contact electrode 22 that physically contacts the heart.

Referring to all figures, it will now be understood that to utilize the defibrillation system 10, the conductive pad 14 is placed under a patient. Using existing access incisions or a newly formed access incision, the paddle head 34 of the overall paddle assembly 20 is advanced in vivo to the heart. Using the handle 28, a physician positions the paddle head 34 against the heart.

The paddle head 34 is flexible and can conform to the contours of the heart. This places the contact electrode 22 flush against the heart. In this manner, the current waveform passing into the heart is evenly distributed across the full area of the contact electrode 22, therein preventing electrical burn damage to the heart.

Most of the paddle head 34 is molded from a thermoplastic elastomer. The conductive elements within the paddle head 34 contain only a small amount of conductive metal. The handle 28 is also a low-cost molded construct.

The most expensive component in terms of fabrication materials is the conductive core element, which is nothing more than a short length of flexible wire. Accordingly, the whole of the paddle assembly 20 can be made near the cost of cleaning, sterilizing, and repackaging a reusable defibrillation paddle. The result is a defibrillation paddle assembly 10 that can be considered disposable and economical for one-time-use.

It will be understood that the embodiment of the present invention that is illustrated and described is merely exemplary and that a person skilled in the art can make many variations to the embodiment. For instance, the shape of the paddle head can be altered for different patients and different needs. The length of the flexible neck can be altered. Likewise, the handle can have many shapes. All such embodiments are intended to be included within the scope of the present invention as defined by the claims.

What is claimed is:

1. A defibrillation paddle assembly, comprising:

a handle;

a flexible paddle extending from said handle, wherein said flexible paddle has a flexible head and a flexible neck unistructurally formed from a thermoplastic elastomer;

a contact electrode attached to said flexible paddle head;

a conductive core element having a first end and an opposite second end, wherein said conductive core element extends through said handle and said flexible neck, wherein said first end of said conductive core element terminates within said flexible paddle head, and said first end of said conductive core element is electrically interconnected to said contact electrode within said flexible paddle head, and a connector disposed within said handle that engages said conductive core element and locks said conductive core element in a fixed position relative to said handle.

2. The assembly according to claim 1, wherein said flexible head of said flexible paddle has a width and can be elastically deformed into a smaller width for insertion into a person's body.

3. The assembly according to claim 1, wherein said conductive core element is flexible.

4. The assembly according to claim 1, wherein said second end of said conductive core element terminates with a wire connector outside of said handle.

5. The assembly according to claim 1, further including a terminal that electrically interconnects said contact electrode to said conductive core element within said flexible paddle head.

6. The assembly according to claim 1, wherein said handle has a first half and a second half that close together around said conductive core element.

7. A defibrillation paddle assembly, comprising:

a flexible paddle having a flexible head and a flexible neck unistructurally molded from a silicone elastomeric material;

a contact electrode supported by said flexible paddle head;

a handle coupled to said flexible paddle head for selectively manipulating said flexible paddle head, wherein said handle has a two-part clamshell design that includes a first half and a second half, wherein said first half and said second half of said handle close around and engage said flexible neck of said flexible paddle, wherein said flexible neck extends concentrically from said handle and acts as a cantilever and self-centering spring in supporting said flexible paddle head at first distance from said handle;

a conductive core element having a first end and an opposite second end, wherein said conductive core element extends through said handle and through said flexible neck, wherein said first end of said conductive core element terminates in said flexible paddle head and said second end of said conductive core element terminates outside said handle, wherein said first end of said conductive core element is electrically coupled to said contact electrode within said flexible paddle head; and a connector disposed within said handle that engages said conductive core element and locks said conductive core element in a fixed position relative to the handle as said first half and said second half of the handle are joined.

8. The assembly according to claim 7, wherein said flexible paddle head has a support pad, wherein said contact electrode is mounted on said support pad.

9. The assembly according to claim 8, wherein said support pad has a width that can be reduced by elastically deformation of said support pad.

10. The assembly according to claim 8, wherein said conductive core element is flexible.

11. The assembly according to claim 10, wherein said second end of said conductive core element terminates with a wire connector outside said handle.

12. The assembly according to claim 8, further including a terminal that electrically interconnects said contact electrode to said conductive core element within said flexible paddle head.

13. The assembly according to claim 12, wherein said handle supports said conductive core element and prevents relative movement of said conductive core element within said handle.

* * * * *